United States Patent [19]
Zirps et al.

[11] Patent Number: 6,048,339
[45] Date of Patent: *Apr. 11, 2000

[54] FLEXIBLE SURGICAL INSTRUMENTS WITH SUCTION

[75] Inventors: Christopher Zirps, Milton; Matthew Emans, Boston; Timothy E. Taylor, Attleboro, all of Mass.

[73] Assignee: Endius Incorporated, Planville, Mass.

[*] Notice: This patent is subject to a terminal disclaimer.

[21] Appl. No.: 09/106,655

[22] Filed: Jun. 29, 1998

[51] Int. Cl.⁷ .................................................. A61M 25/00
[52] U.S. Cl. ......................... 604/525; 604/523; 604/533; 604/264; 600/433; 600/585
[58] Field of Search .............................. 604/35, 525, 528, 604/264, 530, 533, 535, 523; 600/433–35, 585

[56] References Cited

U.S. PATENT DOCUMENTS

| | | |
|---|---|---|
| 5,669,926 | 9/1997 | Aust et al. |
| 5,851,212 | 12/1998 | Zirps et al. ............................ 606/167 |
| 5,911,715 | 6/1999 | Berg et al. ............................ 604/525 |

*Primary Examiner*—Ronald Stright
*Assistant Examiner*—Patricia M Bianco

*Attorney, Agent, or Firm*—Tarolli, Sundheim, Covell, Tummino & Szabo L.L.P.

[57] ABSTRACT

A surgical instrument (10) includes a rigid stem section (12) defining a longitudinal axis (32) of the surgical instrument. The rigid stem section (12) has a central passage (86) for aspirating human tissue through the rigid stem section. A flexible stem section (14) extends from the rigid stem section (12). The flexible stem section (14) has a central passage (86) for aspirating human tissue through the flexible stem section. The flexible stem (14) section has a distal end portion (68) defining a suction opening (74) of the surgical instrument (10). The suction opening (74) communicates with the central passage (86) of the flexible stem section (14). The flexible stem section (14) comprises a bendable outer tubular member (60) and a bendable inner tubular member (90) slidable within the outer tubular member. The outer tubular member (60) has a neutral axis of bending (66). The inner tubular member (90) has a neutral axis of bending (102) spaced apart from the neutral axis of bending (66) of the outer tubular member (60). The flexible stem section (14) is movable between a plurality of orientations relative to the axis (32) in response to relative sliding movement between the inner and outer tubular members (90, 60).

5 Claims, 3 Drawing Sheets

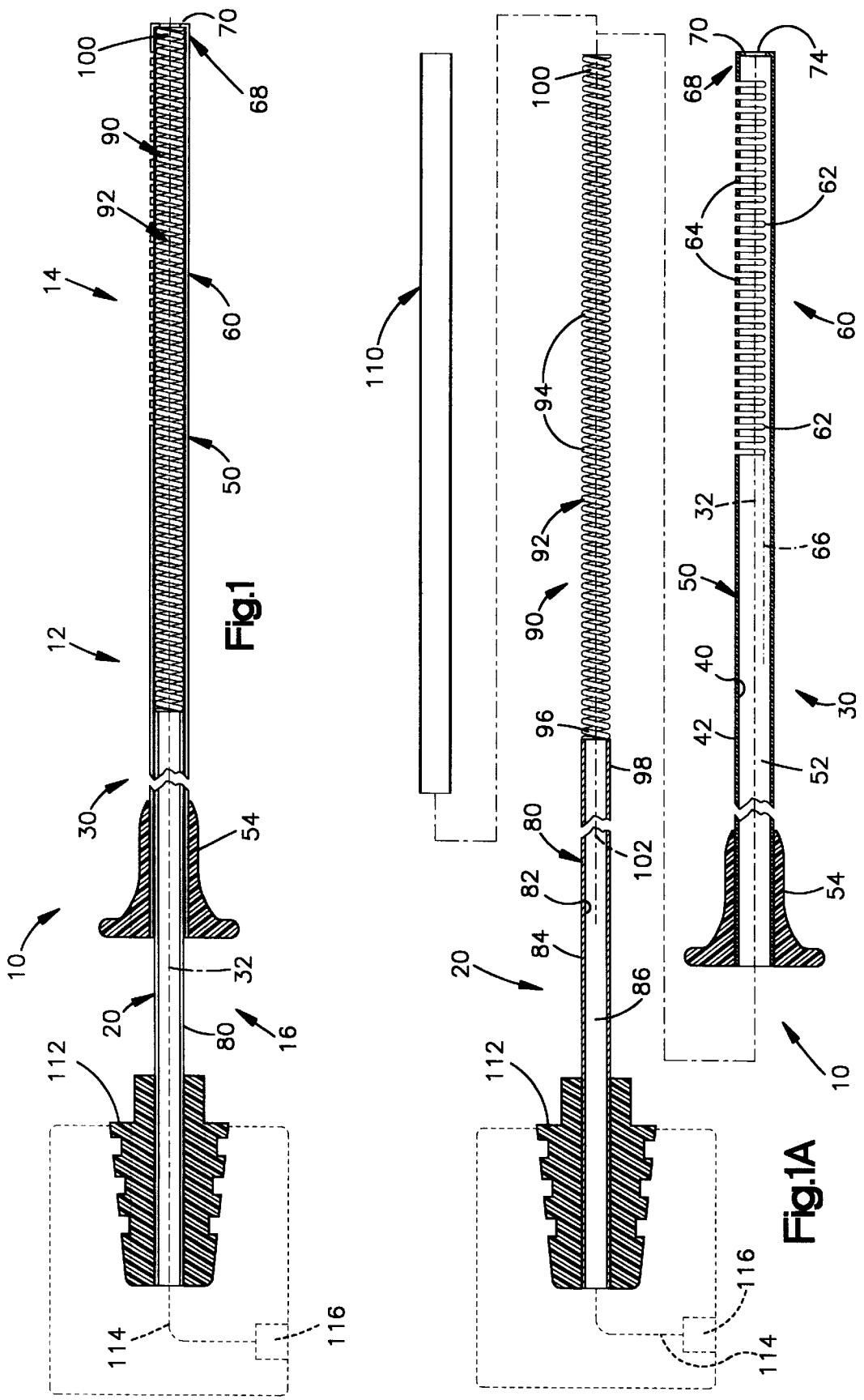

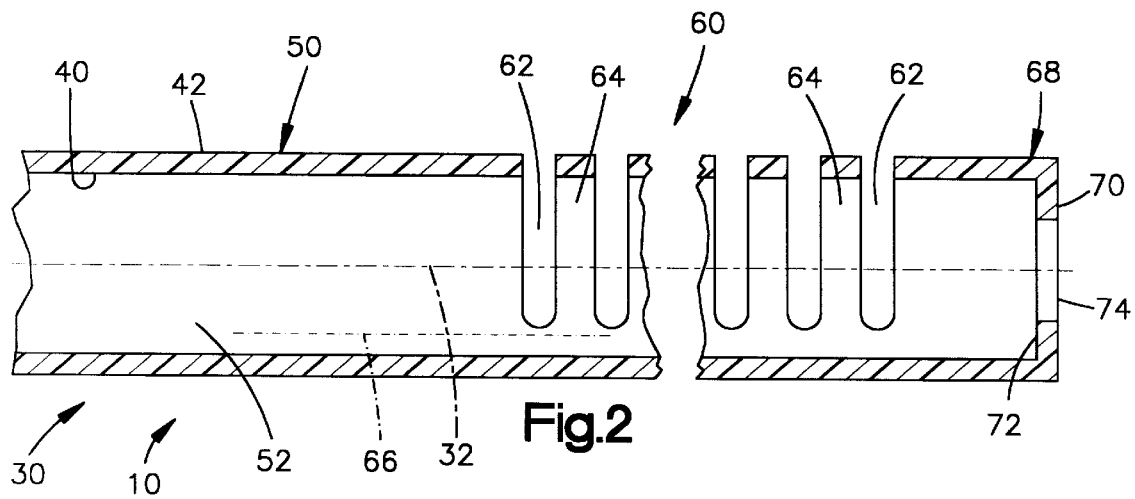
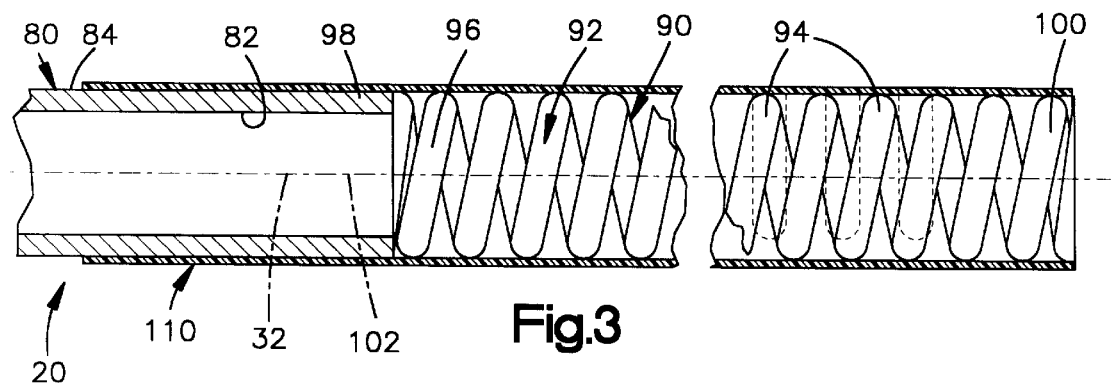
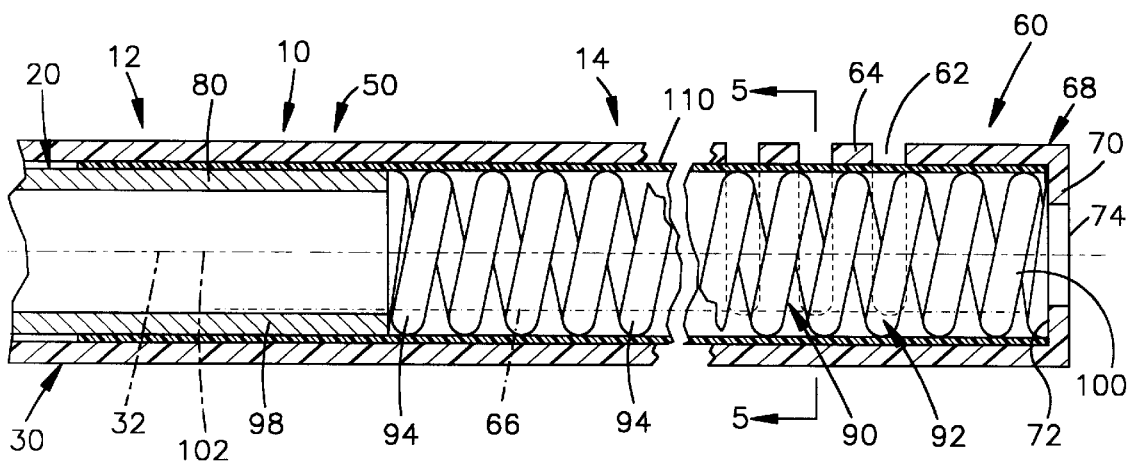

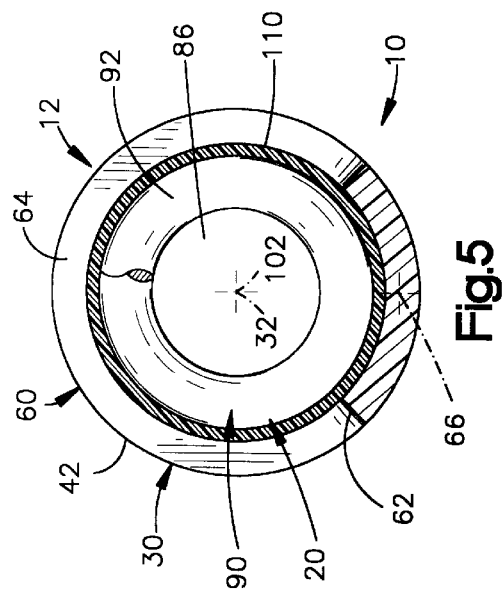
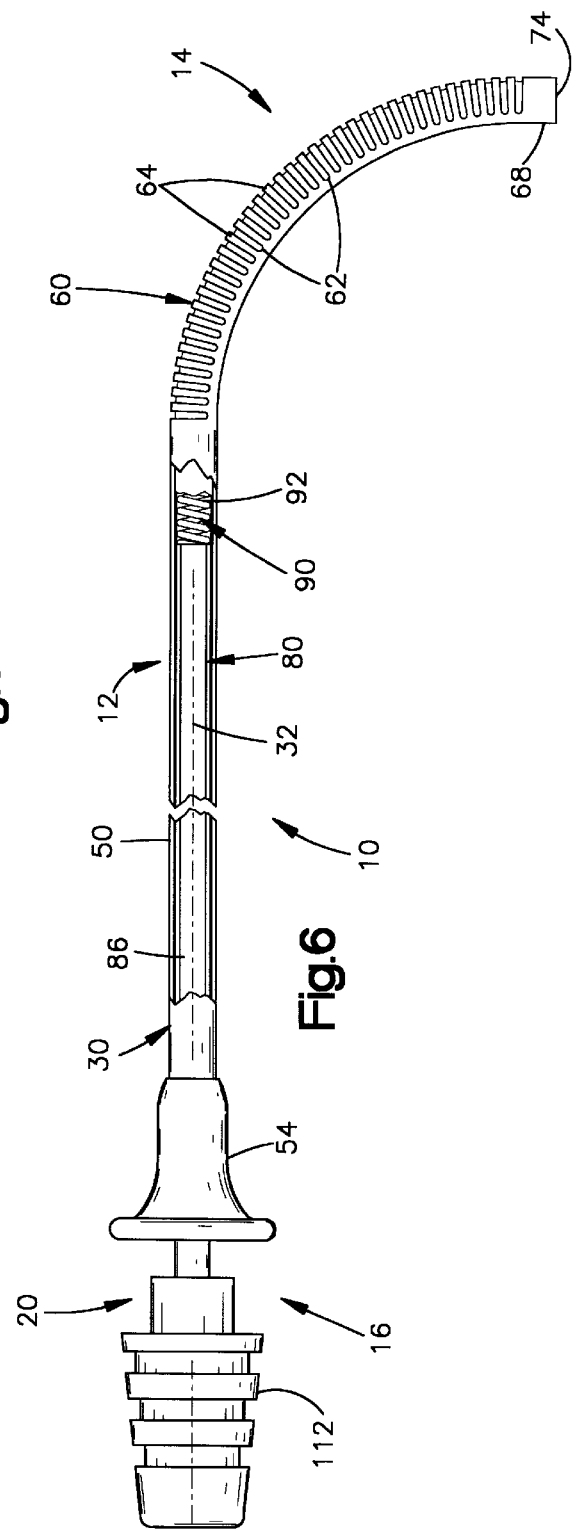

FLEXIBLE SURGICAL INSTRUMENTS WITH SUCTION

BACKGROUND OF THE INVENTION

The present invention relates to a surgical instrument and, more particularly, to a flexible endoscopic surgical instrument which may be used for suction of human tissue.

SUMMARY OF THE INVENTION

The present invention is a surgical instrument comprising a rigid stem section defining a longitudinal axis of the surgical instrument. The rigid stem section has a central passage for aspirating human tissue through the rigid stem section. The instrument also comprises a flexible stem section extending from the rigid stem section, the flexible stem section having a central passage for aspirating human tissue through the flexible stem section. The flexible stem section has a distal end portion defining a suction opening of the surgical instrument, the suction opening communicating with the central passage of the flexible stem section. The flexible stem section comprises a bendable outer tubular member and a bendable inner tubular member slidable within the outer tubular member. The outer tubular member has a neutral axis of bending. The inner tubular member has a neutral axis of bending spaced apart from the neutral axis of bending of the outer tubular member. The flexible stem section is movable between a plurality of orientations relative to the axis in response to relative sliding movement between the inner and outer tubular members.

BRIEF DESCRIPTION OF THE DRAWINGS

Further features of the present invention will become apparent to those skilled in the art to which the present invention relates from reading the following specification with reference to the accompanying drawings, in which:

FIG. 1 is a side elevational view, partly in section, of a surgical instrument constructed in accordance with a first embodiment of the present invention;

FIG. 1A is an exploded view of the parts of the surgical instrument of FIG. 1;

FIG. 2 is an enlarged view of a flexible stem section of an outer tube of the surgical instrument of FIG. 1, shown in a linear condition;

FIG. 3 is an enlarged view of a flexible stem section of an inner tube of the surgical instrument of FIG. 1, shown in a linear condition;

FIG. 4 is an enlarged view of a flexible stem section of the surgical instrument of FIG. 1, showing both the inner and outer tubes;

FIG. 5 is a sectional view taken along line 5—5 of FIG. 4; and

FIG. 6 is a view similar to FIG. 1 showing the flexible stem section of the surgical instrument in a curved condition.

DESCRIPTION OF A PREFERRED EMBODIMENT

The present invention relates to a surgical instrument and in particular to an endoscopic surgical instrument which may be used for suctioning of human tissue. The present invention is applicable to various surgical instrument constructions. As representative of the present invention, FIGS. 1 illustrates a surgical instrument 10.

The surgical instrument 10 has a rigid stem section 12, a flexible stem section 14, and a deflection control assembly 16 for controlling bending movement of the flexible stem section. The surgical instrument 10 includes an inner tubular member or inner tube 20, and an outer tubular member or outer tube 30. The tubes 20 and 30 are coaxial and are centered on a longitudinal central axis 32 of the instrument 10 when the instrument is in a linear condition as shown in FIG. 1. The inner and outer tubes 20 and 30 are relatively slidable to effect bending movement of the flexible stem section 14 to a condition off the axis 32, as shown in FIG. 6, for example.

The outer tube 30 (FIGS. 1A and 2) is made from a resilient plastic material. The outer tube 30 has a cylindrical configuration including parallel inner and outer side surfaces 40 and 42.

The outer tube 30 includes a proximal or rigid stem section 50 which is substantially non-bendable during use of the surgical instrument 10. The rigid stem section 50 of the outer tube 30 has a tubular cylindrical configuration centered on the axis 32. The rigid stem section 50 of the outer tube 30 defines a cylindrical central passage 52. The rigid stem section 50 of the outer tube 30 has a uniform configuration around its circumference and, therefore, its neutral axis of bending is located at the radial center of the outer tube.

A first handle portion 54, part of the deflection control assembly 16, is located on the proximal end of the outer tube 30. The first handle portion 54 is configured to enable the user to pull proximally on the outer tube 30.

The outer tube 30 is weakened at predetermined locations along its distal portion to form a flexible stem section 60 of the outer tube. The flexible stem section 60 of the outer tube 30 is formed as one piece with the rigid stem section 50. Specifically, a series of up to twenty or more openings or slots 62 are formed in the upper (as viewed in FIGS. 2 and 3) sector of the outer tube 30. Each one of the slots 62 has a circumferential extent of about 250°.

The slots 62 define a series of relatively movable links 64. The links 64 are the sections of the outer tube 30 which are located axially between adjacent slots 62. The slots 62 act as pivot joints or pivot axes between the links 64. The links 64 are pivotally interconnected by the material of the outer tube 30 which is not cut away at the slots 62. The pivotal interconnection of the links 64 enables controlled movement of the flexible stem section 60 to a plurality of positions off the axis 32.

The slotting of the outer tube 30 varies the bending resistance of the flexible stem section 60 of the outer tube in a predetermined manner. Specifically, the bending resistance of the outer tube 30 and, thereby, of the flexible stem section 60, is decreased at the location of each one of the slots 62. Because the slots 62 do not extend completely around the circumference of the outer tube 30, the neutral axis of bending of the flexible stem section 60 of the outer tube 30 is located at the material of the outer tube which is not cut away at the slots, generally in the area indicated at 66 in FIG. 2).

The outer tube 30 has a distal end portion 68. The distal end portion 68 includes an annular lip 70 which extends radially inward from the inner side surface 40. The lip 70 has an annular, radially extending, axially inner side surface 72. The lip 70 defines a suction opening 74 which opens into a central passage 76 of the outer tube 30.

The inner tube 20 (FIGS. 1A and 3) includes a rigid stem section 80. The rigid stem section 80 is made from a rigid material such as stainless steel. The rigid stem section 80 has a cylindrical configuration including parallel, cylindrical inner and outer side surfaces 82 and 84 centered on the axis 32. The inner side surface 82 partially defines a cylindrical central passage 86 of the inner tube 20. The rigid stem section 80 of the inner tube 20 is located inside the rigid stem section 50 of the outer tube 30.

The inner tube 20 of the surgical instrument 10 has a flexible stem section 90. The flexible stem section 90 of the inner tube 20 is received within the flexible stem section 60 of the outer tube 30.

The flexible stem section 90 of the inner tube 20 comprises a spring 92. In the illustrated embodiment, the spring 92 is a coiled extension spring, specifically, a cylindrical helical spring, made from metal wire having a circular cross section. The spring 92 is preferably made from stainless steel. The spring 92 partially defines the central passage 86 of the inner tube 20.

The spring 92 includes a plurality of coils 94 spaced along the length of the flexible stem section 90. A proximal or first end portion 96 of the spring 92 is secured, as by welding, to a distal end portion 98 of the rigid stem section 80 of the inner tube 20. An opposite distal or second end portion 100 of the spring 92 is disposed radially inward of the distal end portion 68 of the outer tube 30.

The spring 92 provides a self-centering effect for the flexible stem section 14 of the surgical instrument 10. Specifically, when the flexible stem section 14 of the instrument 10 is bent to a condition off the axis 32, as described below, the resilience provided by the spring 92 returns the flexible stem section to its linear position upon release of the bending force. The inner tube 20 has a uniform configuration around its circumference and, therefore, its neutral axis of bending 102 is located at the radial center of the inner tube.

The inner tube 20 of the surgical instrument 10 includes a plastic outer sheath indicated schematically at 110. The sheath 110 is in the form of a shrink wrap which overlies the spring 92 and a portion of the rigid stem section 80 of the inner tube 20. The sheath 110 seals the openings between adjacent coils 94 of the spring 92. The sheath 110 is, for clarity, shown with an exaggerated thickness in FIG. 3.

A second handle portion 112, part of the deflection control assembly 16, is located on the proximal end of the inner tube 20. The second handle portion 112 of the inner tube 20 includes passage means 114 for connecting the central passage 86 of the inner tube in fluid communication with a source of suction indicated schematically at 116.

To effect bending movement of the flexible stem section 14 of the instrument 10, the inner tube 20 is moved (slid) axially relative to the outer tube 30. For example, to bend the surgical instrument 10 as shown in FIG. 7, the first handle portion 54 of the outer tube 30 is grasped manually and pulled toward the second handle portion 112 of the inner tube 20. The lip 70 on the distal end portion 68 of the outer tube 30 engages the distal end portion 100 of the inner tube 20. Specifically, the annular surface 72 on the lip 70 engages the distal end portion 100 of the spring 92 of the inner tube 20.

The force of the axially moving outer tube 30 is transmitted into the distal end portion 100 of the extension spring 92. This force attempts to compress the spring 92 axially. The spring 92 does compress, but not linearly. Instead, because the slots 62 of the outer tube 30 place the neutral axis 66 of bending of the outer tube 30 away from the neutral axis of bending 102 of the spring 92, the flexible stem section 14 bends as it compresses, to the condition shown in FIG. 6.

The unslotted side (at the neutral axis of bending 66) of the outer tube 30 neither compresses nor extends. The flexible stem section 60 of the outer tube 30 extends axially along its slotted side. The flexible stem section 90 of the inner tube 20 bends in the same direction as the outer tube 30, along its neutral axis of bending 102.

The bending of the flexible stem section 14 causes the distal end portion of the surgical instrument 10 to be moved to an orientation off the longitudinal central axis 32. The amount of bending movement of the flexible stem section 14, and, thus, the position or orientation of the suction opening 74, is controlled by the amount of relative axial displacement between the inner and outer tubes 20 and 30. If the outer tube 30 is displaced axially relative to the inner tube 20 by a relatively small amount or distance, the amount of bending movement of the flexible stem section 14 is relatively small, and the suction opening 74 assumes an orientation relatively close to the longitudinal central axis 32. If, on the other hand, the outer tube 30 is displaced axially relative to the inner tube 32 by a relatively large amount or distance, the amount of bending movement of the flexible stem section 14 is relatively large, and the suction opening 74 assumes an orientation relatively far from the longitudinal central axis 32.

In the illustrated embodiment, the suction opening 74 is selectively movable to any orientation up to 90° off the longitudinal central axis 32. It should be understood that the present invention is not limited to bending movement of 90°.

The distal end portion 100 of the spring 92 is, preferably, glued or otherwise adhered to the distal end portion 68 of the outer tube 30. If this is done, then axially outwardly directed force on the outer tube 30 can be transmitted into the inner tube 20. Thus, when the outer tube 30 is pushed outward relative to the inner tube 20 (to the right as viewed in FIG. 1), the flexible stem section bends 14 in the opposite manner (not shown).

Upon movement of the handle portions 54 and 112 to their initial position, the axial force on the inner and outer tubes 20 and 30 is released. The resilience provided by the spring 92 returns the surgical instrument 10 to its linear position.

Suction is applied to the instrument 10 through the central passage 86 in the inner tube 20. The suction draws or pulls tissue from the area immediately adjacent to the suction opening 74 back through the center of the flexible stem section 14 and through the center of the rigid stem section 12, to a point where it can be removed. The sheath 110 seals the openings in the spring section 92 of the inner tube 20 and keeps suctioned matter from exiting the surgical instrument 10 at any undesired location.

In addition, water or other fluid can be utilized to irrigate the area of the suction opening 74. The irrigation fluid can be conducted through the central passage 86 in the inner tube 20, to the distal end portion 68 of the surgical instrument.

It should be understood that the handle portions 54 and 112, which control the deflection of the surgical instrument 10 off the axis, are illustrated only schematically. Other types of deflection control assemblies can be substituted. Thus, the deflection control assembly 16 is illustrative of the various types of deflection control assemblies which can be used to provide the force for bending the flexible stem section 14 of the surgical instrument 10 in the manner illustrated.

From the above description of the invention, those skilled in the art will perceive improvements, changes and modifications in the invention. Such improvements, changes and modifications within the skill of the art are intended to be covered by the appended claims.

Having described the invention, we claim:

1. A surgical instrument comprising:

a rigid stem section defining a longitudinal axis of said surgical instrument, said rigid stem section having a central passage for aspirating human tissue through said rigid stem section; and a flexible stem section extending from said rigid stem section, said flexible stem section having a central passage for aspirating human tissue through said flexible stem section;

said flexible stem section having a distal end portion defining a suction opening of said surgical instrument, said suction opening communicating with said central passage of said flexible stem section;

said flexible stem section comprising a bendable outer tubular member and a bendable inner tubular member compressible within said outer tubular member, said outer tubular member having a neutral axis of bending, said inner tubular member having a neutral axis of bending spaced apart from the neutral axis of bending of said outer tubular member;

said flexible stem section being movable between a plurality of orientations relative to said axis in response to relative compressing movement between said inner and outer tubular members;

said bendable outer tubular member being made from a resilient material having a plurality of slots defining a series of relatively movable links, each one of said slots having a circumferential extent of less than 360 degrees, the neutral axis of bending of said bendable outer tubular member being located generally at the material of said outer tubular member which is not cut away at said slots;

said bendable inner tubular member comprising a coiled spring having a neutral axis of bending located on said longitudinal axis of said surgical instrument;

wherein said distal end portion of said flexible stem section includes an annular lip on said outer tubular member that extends radially inward from an inner side surface of said outer tubular member, said lip having an annular, radially extending, axially inner side surface that defines said suction opening.

2. A surgical instrument as set forth in claim 1 wherein a distal end portion of said inner tubular member is glued or otherwise adhered to a distal end portion of said outer tubular member to enable transmission of axially outwardly directed force on said outer tubular member into said inner tubular member.

3. A surgical instrument as set forth in claim 2 further comprising a sheath on said coiled spring for sealing between adjacent turns of said coiled spring.

4. A surgical instrument as set forth in claim 3 wherein each one of said slots has a circumferential extent of about 250 degrees.

5. A surgical instrument as set forth in claim 1 wherein a distal end portion of said inner tubular member is glued or otherwise adhered to a distal end portion of said outer tubular member to enable transmission of axially outwardly directed force on said outer tubular member into said inner tubular member.

* * * * *